(12) United States Patent
Griesbach et al.

(10) Patent No.: US 6,767,509 B1
(45) Date of Patent: Jul. 27, 2004

(54) SELF-STERILIZING PACKAGING

(75) Inventors: Henry L. Griesbach, Clarkston, GA (US); Peter N. Gray, Chicago, IL (US)

(73) Assignees: Kimberly-Clark Worldwide, Inc., Neenah, WI (US); Bernard Technologies, Inc., Chicago, IL (US)

( * ) Notice: Subject to any disclaimer, the term of this patent is extended or adjusted under 35 U.S.C. 154(b) by 476 days.

(21) Appl. No.: 09/592,034

(22) Filed: Jun. 12, 2000

Related U.S. Application Data

(60) Provisional application No. 60/139,681, filed on Jun. 16, 1999.

(51) Int. Cl.[7] .................................................. A61L 2/00
(52) U.S. Cl. .............................. 422/29; 422/28; 422/34; 422/37; 422/40; 422/292; 422/294; 422/300; 422/306
(58) Field of Search .............................. 422/29, 78, 34, 422/37, 40, 292, 294, 300, 306

(56) References Cited

U.S. PATENT DOCUMENTS

| | | |
|---|---|---|
| 3,084,793 A | 4/1963 | Pitman |
| 3,346,464 A | 10/1967 | Ernst |
| 3,440,144 A | 4/1969 | Anderson |
| 3,704,096 A | 11/1972 | Verses |
| 3,752,743 A | 8/1973 | Henshilwood |
| 3,977,945 A | 8/1976 | Tornmarck |
| 4,015,937 A | 4/1977 | Miyamoto |
| 4,091,921 A | 5/1978 | Lewis |
| 4,121,714 A | 10/1978 | Daly |
| 4,205,043 A | 5/1980 | Esch |
| 4,206,844 A | 6/1980 | Thukamoto |
| 4,235,332 A | 11/1980 | Andersen |
| 4,248,597 A | 2/1981 | McNeely |
| 4,287,306 A | 9/1981 | Brewer |
| 4,298,569 A | 11/1981 | Read |
| 4,580,682 A | 4/1986 | Gorski |
| 4,717,661 A | 1/1988 | McCormick |
| 4,741,437 A | 5/1988 | Gorski |
| 4,743,537 A | 5/1988 | McCormick |
| 5,126,070 A | 6/1992 | Leifheit |
| 5,317,987 A | 6/1994 | Muller |
| 5,344,017 A | 9/1994 | Wittrock |
| 5,374,394 A | 12/1994 | Kralovic |
| 5,439,648 A | 8/1995 | Balderson |
| 5,443,987 A | 8/1995 | DeCicco |
| 5,486,459 A | 1/1996 | Burnham |
| 5,498,526 A | 3/1996 | Caputo |
| 5,549,924 A | 8/1996 | Shlenker |
| 5,620,656 A | 4/1997 | Wensky |
| 5,631,300 A | 5/1997 | Wellinghoff |
| 5,650,446 A | 7/1997 | Wellinghoff |
| 5,688,476 A | 11/1997 | Bourne |
| 5,695,814 A | 12/1997 | Wellinghoff |
| 5,699,326 A | 12/1997 | Haas |
| 5,705,092 A | 1/1998 | Wellinghoff |
| 5,733,503 A | 3/1998 | Kowatsch |
| 5,739,004 A | 4/1998 | Woodson |
| 5,744,321 A | 4/1998 | Harewood |

*Primary Examiner*—Krisanne Thornton
(74) *Attorney, Agent, or Firm*—Nelson Mullins Riley & Scarborough

(57) ABSTRACT

A sterilization system and process is provided which is useful in the chemical sterilization of medical supplies and equipment. The system includes a container having an internal generator of a sterilant such as chlorine dioxide. An internal container activator, such as high humidity or manual manipulation, is provided and stimulates the formation and release of the sterilant. The package includes a first indicator responsive to the release of sterilant and a second indicator which records the passage of a predetermined time interval. The combination of the sterilant indicator and the time interval indicator signals that proper sterilization conditions have been met and that the objects have been suitably sterilized.

27 Claims, 2 Drawing Sheets

SELF-STERILIZING PACKAGING

The present invention is based on provisional patent application Ser. No. 60/139,681 filed Jun. 16, 1999, and priority is hereby claimed therefrom.

FIELD OF THE INVENTION

This invention relates to a process and apparatus for chemical sterilization of objects such as medical supplies, instruments and similar articles. More specifically, the invention relates to self-sterilizing packages for housing medical instruments and other sterilizable objects.

BACKGROUND OF THE INVENTION

Many of the medical supplies and surgical instruments used in an operating room or examination room are reusable. These supplies may include such things as clamps, scalpel blade handles, retractors, forceps, scissors, towels, and surgical garments.

Such items must be collected following each medical procedure, cleaned, and sterilized before they can be used again. To this end, the materials are prepared for sterilization by placing them into various packages including rigid trays, flexible pouches, and other common sterilizable packaging. If flexible pouches are used, the instruments or other objects are enclosed within a pouch that will be sealed around the materials. The pouch may be constructed from various materials that are permeable to a sterilizing medium so as to permit a medium such as a sterilizing vapor or gas to pervade through the pouch and sterilize the enclosed materials. If trays or other more rigid packaging is employed, such structures may be covered with a sterilization wrap and then sealed so that the materials to be sterilized are sealed within the wrapped enclosure. Like the pouches, the sterilization wrap will be permeable to a sterilizing medium. In addition to providing a holder in which to contain and sterilize the medical materials, such sterilization wraps and pouches also provide a transportable, protective barrier against contaminants following sterilization.

Typically, sterilization of medical supplies makes use of a dedicated facility and equipment to supply an external sterilant, or sterilizing medium, which may often be in the form of pressurized steam or ethylene oxide. The sterilant permeates a pouch, wrap, or other enclosure material, or is pumped into the interior of the package, and sterilizes the contents held therein. Following sterilization, the pouch or wrapping maintains the sterility of the respective contents during subsequent handling and transport of the package and contents. Thereafter, the package may be opened using aseptic techniques to access the package contents.

A description of one such sterilization process utilizing sterilization wrap materials is disclosed in U.S. Pat. No. 5,688,476 to Bourne et al. which is owned by the assignee of the present invention and which is incorporated herein by reference in its entirety. Various pouches into which articles may be enclosed for sterilization in either a wrapped or an unwrapped state are shown in U.S. Pat. Nos. 4,121,714 to Daly et al. 4,206,844 to Thukamoto et al., 5,344,017 to Wittrock, and 5,620,656 to Wensky et al. Such pouches may employ indicators which visually signal that the package has been subjected to a sterilization protocol. However, such pouches have been adapted for being subjected to an eternally-supplied sterilizing agent, such as ethylene oxide, that must penetrate the pouch to bring about internal sterilizing conditions within the pouch or other compartment.

In addition, there is growing concern over worker exposure to certain chemical sterilizing agents such as ethylene oxide. Thus, the development of other sterilizing agents would be beneficial. One alternative sterilizing agent is chlorine dioxide ($ClO_2$). This particular sterilant gas is a strong oxidizer and acts as a broad spectrum biocide for bacteria, fungi, viruses, and algae. The efficacy of chlorine dioxide is similar to that of ethylene oxide. In particular, chlorine dioxide is effective at killing bacterial spores. Chlorine dioxide has a high affinity for water which contributes to its ability to kill water-containing microorganisms. However, chlorine dioxide does not have the carcinogenic properties of ethylene oxide.

Additionally, U.S. Pat. No. 3,704,096 to Verses et al. teaches the use of ozone as an internally-contained sterilizing agent. Verses et al. provides a sterilizable package in which an ozone sterilizing mist is introduced to the package followed by sealing of the package. Verses et al. requires tumbling or other agitation of the package to achieve adequate sterilization.

Accordingly, there remains a need for a reliable sterilization system which does not require dedicated equipment or personnel. Further, there remains a need for a sterilization system in which the sterilizing conditions are supplied from within the interior of a sealed sterilization pouch or other sterilization container. Such a system would offer an option to existing chemical and steam sterilization procedures. Further, the system would provide for increased mobility, field use, and as a back-up system for existing protocols which rely upon an external supply of sterilant.

As will be seen from the description and illustrations to follow, none of the above-identified references disclose or anticipate the present invention.

SUMMARY OF THE INVENTION

The present invention is directed to a sterilization compartment or package that is capable of being "self-sterilized". "Self-sterilized" and "self-sterilizable" as used herein refers to packages that have the capability of bringing about sterilization conditions inside an enclosed container without the necessity of being treated with an externally-supplied sterilizing medium. In fact, in certain embodiments, the boundaries of the enclosed container are formed from a substantially fluid-impermeable material so that the sterilization conditions can be maintained within the container for a period of time. These self-sterilizable packages may be desirable for use in health-care facilities that do not have high capacity, large volume sterilization systems. Such large volume systems typically require workers trained to operate the sterilization equipment and require capital expenditures to acquire and maintain the equipment. Self-sterilizable packages provide an attractive alternative for small volume users who may be unwilling to devote the space or resources required for using a typical autoclave or chemical sterilization system. Even beyond the expense aspect, self-sterilizable packaging provides advantages to those who do have the resources to employ large volume sterilization systems. For example, such self-sterilizable packages would require less energy for sterilization, require less handling of the package which influences the propensity for breaching the sterilized conditions, etc.

The present invention recognizes and addresses some of the limitations of prior art sterilization processes and apparatuses. A useful self-sterilizing system can be provided by employing a container having an interior and a sealable opening through which an object may be placed into the interior of the container. A sterilant generator, such as a solid state chemical system that releases chlorine dioxide (although any internal sterilant generator may be employed), is disposed within the container. The container is also equipped with an indicator adapted to indicate when sterilizing conditions have been achieved within the container after it is sealed and self-sterilization has begun. The indicator may take the form of an indicator that indicates the start of sterilant release or the level of sterilant achieved within the container. In addition, the indicator may be a time indicator that indicates the passage time after sealing of the container or beginning of sterilant release.

In the present process, when an object is placed within the interior of the container, the opening of the container may be sealed. The sterilant generator is then activated to release an effective amount of sterilant within the interior of the container to sterilize the objects therein. The indicator associated with the package will then indicate the presence of sterilizing conditions and/or the passage of time.

One type of useful generator for the present invention releases chlorine dioxide gas. The generator may be activated by an appropriate trigger mechanism such as a humid environment which will initiate the release of a predetermined amount of chlorine dioxide.

A sensor responsive to the released chlorine dioxide may signal the successful release of an effective amount of the sterilant within the container. An additional time indicator may also be used to verify that a predetermined time interval has elapsed since sealing of the container or initial release of the sterilant. The release of sterilant and its presence over a sufficient time interval results in sterilization of the package contents.

The present invention enables various types of materials including tubing, fabrics, endoscopes, devices or materials having extensive lumens and internal cavities, and/or heat sensitive materials to be sterilized. Such materials require a sufficiently long duration of exposure to the chemical sterilizing agent that all portions of the materials are exposed to an effective amount of the sterilant. Accordingly, the combination of a sterilant indicator, which qualitatively reflects the release of a sterilization agent, with a time indicator, which quantitatively indicates a sufficient passage of time, work together to provide verification that sterilization has occurred.

These and other features, aspects and advantages of the present invention will become better understood with reference to the following description and appended claims.

BRIEF DESCRIPTION OF THE DRAWINGS

A full and enabling disclosure of the present invention, including the best known mode thereof, to one of ordinary skill in the art, is set forth more particularly in the remainder of the specification, including reference to the accompanying drawings.

Figure 1A:
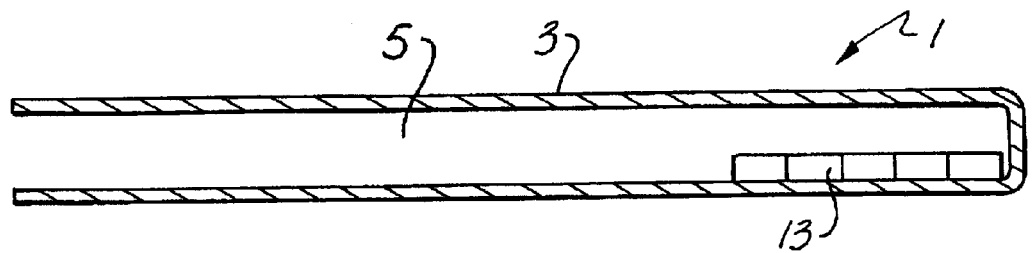
FIGS. 1A–1D are diagrammatic representations of a flexible container for a sterilization package in accordance with the present invention.

DETAILED DESCRIPTION OF A
REPRESENTATIVE EMBODIMENT

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

In general, the present invention relates to a process and apparatus which permits the chemical self-sterilization of medical supplies within an enclosed package.

As used herein, "medical supplies" refers to medical articles which routinely require sterilization. This may include items such as stainless steel instrumentation, intravenous tubing, endoscopes, surgical gowns, operating room towels and wipes, and similar articles.

The term "sterilizing conditions" refers to a combination of a concentration of sterilant and a time exposure interval which will sterilize an object which is subjected to a sterilant within a sterilizing container. Sterilizing conditions may be provided by a wide range of sterilant concentrations in combination with various time intervals. In general, the higher the concentration of a sterilant, the shorter a corresponding time interval is needed to establish sterilizing conditions. Accordingly, the effective amount of a sterilant may vary depending upon the length of exposure of the medical supplies to the sterilant.

As used herein "effective amount" may refer to either an amount of sterilant provided to a sterilizing container or a time during which the sterilant has been provided to a sterilizing container to achieve sterilizing conditions. As will be recognized, an effective amount of sterilant depends on the relationship between the amount of sterilant utilized and the time period during which it is utilized. For example, when sterilizable objects are subjected to lengthy periods of sterilization, less amounts of sterilant may be effective in achieving a sterilized object. When sterilizable objects are subjected to large amounts of sterilant, shorter exposure time periods might be appropriate to sterilize such objects.

One embodiment of the present invention is shown in FIGS. 1A to 1D. Sterilization system 1 includes a container as seen in the form of a flexible bag 3 which provides an enclosable interior 5. Bag 3 may be made in certain embodiments by coextruding a 2 millimeter thick layer of plastic comprising polyethylene (PE) & ethylene-vinyl alcohol (EVOH). EVOH provides a barrier layer to retard the passage of a sterilant gas from within the container's interior to the exterior after the container has been subjected to sterilizing conditions. However, variations in container thickness, composition, and the use of other barrier materials are envisioned. In addition, the container may be completely fluid-impermeable, substantially fluid-impermeable, or only moderately fluid-impermeable.

A sterilant indicator 13 is placed within the bag 3 and will provide a visible indication upon exposure to an effective amount of a sterilant. In one particular embodiment, when chlorine dioxide is employed as the sterilization agent, the sterilant indicator may be a chlorine indicator strip which detects the presence of chlorine dioxide gas. Although various types of indicators may be employed, most common indicators undergo a modification in the presence of a sterilant that causes the indicator to demonstrate a visual change.

Such visual sterilant indicators will typically exhibit a color change along or on an indicator strip. For example, an indicator strip may change from white to black or dark blue to signal the presence of chlorine. An example of this type of indicator is depicted in FIG. 1C where the sterilant indicator is shown as incurring a color change on at least one of its visible surfaces. FIGS. 1A through 1D illustrate the gradual change of the color of the sterilant indicator 13. Although in these figures, the sterilant indicator 13 is depicted in full and exhibits a color change over its entire outer surface, the sterilant indicator 13 may be in sections so that a change in color occurs gradually over the length of the indicator. It is also possible to provide a graduated series of color indicators that change in color and intensity as the level of exposure to sterilant increases.

Sterilant indicator 13 may also be composed of multiple indicia materials that are responsive to varying concentrations of sterilants such as chlorine dioxide. One such indicator is shown in U.S. Pat. No. 4,205,043 to Esch et al. which is incorporated herein in its entirety by reference thereto. As set forth in Esch et al., a paper disk may be impregnated with a color sensitive gas indicator chemical that can be selectively activated by the removal of a pressure-sensitive tape covering. Esch et al. explains that the presence and concentration of chlorine dioxide is indicated by a change in color of the indicator.

When exposed to the sterilant, the indicator employed should exhibit a substantially permanent color change to avoid potential confusion when interpreting the indicator results. A sterilant such as chlorine dioxide, which is a known bleaching agent, creates a permanent color modification to the indicators described herein.

Figure 1B:
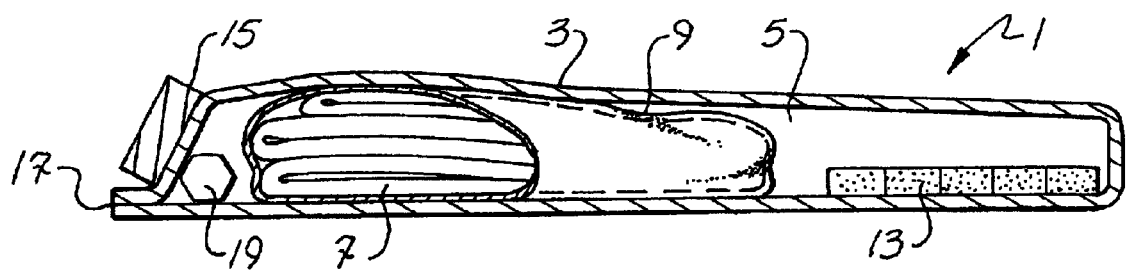
Figure 1C:
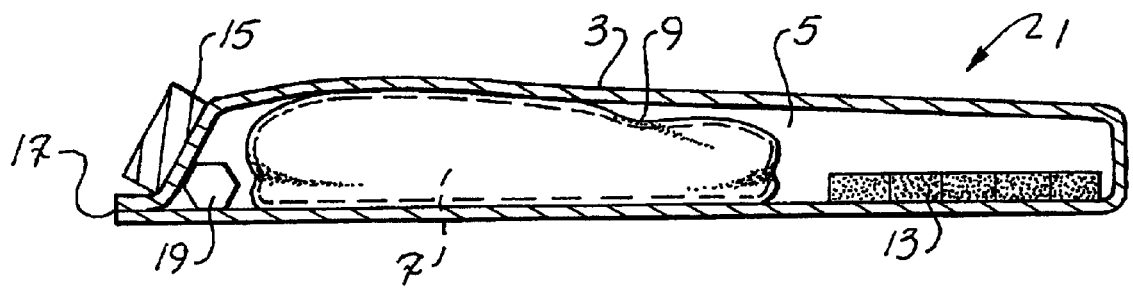
Figure 1D:
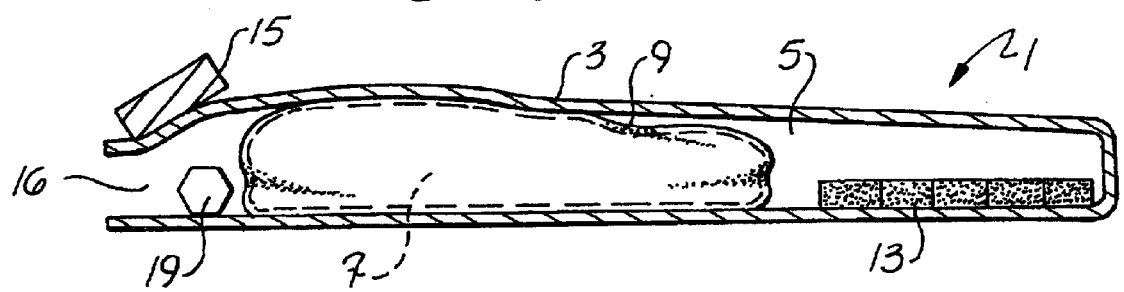

To effect sterilization, a sterilizable article 7, such as a folded surgical gown, is positioned inside bag 3 (FIG. 1B). The sterilizable article 7 may, in some embodiments, be at least partially surrounded by a sterilant generator 9 (such as a chlorine dioxide generating material). In other embodiments, the sterilant generator 9 may be placed separately inside bag 3 and remain unattached to sterilizable article 7.

In addition to the sterilizable article, a sterilant activator 19 is also placed within bag 3. This sterilant activator may be in the form of a humidifier which will provide a moist environment within the sealed bag 3 to trigger release of the sterilant. The activator 19 may be a moistened filter paper, a porous media containing a super-saturated solution of ammonium sulfate, a fabric pad or web holding a supply of water, a device that directly releases a water spray mist within the package interior, or other apparatus or method designed to provide a moist environment.

The bag opening 16 is then sealed, for example, by securing the opening between two overlapping margins to form a seal 17 as shown in FIG. 1B. Seal 17 may be a heat seal, a pressure adhesive seal, a reclosable "zipper type" seal, or the like. As will be clear from the disclosure, the invention is not limited to the particular type of sterilizing container or to the particular type of seal with which the container is sealed. Various forms of containers and seal may be utilized depending on the characteristics of the objects to be sterilized, the available storage facilities for sterilized containers, the particular requirements of the sterilization conditions, etc.

A time indicator 15 may also be provided in conjunction with bag 3. Typically, the user will activate the time indicator at some point after the bag 3 is sealed and upon the sterilant generator 9 being activated. In one particular embodiment, the time indicator 15 may be in proximity to the opening 16. This location serves as a reminder to activate the time indicator and to verify the elapsed time interval prior to removing articles from the sterilization package. Various types of time indicators including clock-like devices, chemical diffusion time indicator strips, etc., may be employed in the present invention.

The sterilant generator 9 useful in the embodiments depicted in FIGS. 1A–1D may be provided in accordance with the teachings of U.S. Pat. No. 5,650,446, which is incorporated herein in its entirety by reference thereto. This particular sterilant generator generates chlorine dioxide gas when activated. A commercial licensee of the above-referenced patent, Bernard Technologies, Inc., treated individual sheets of a nonwoven spunbond-meltblown-spunbond fabric (hereinafter "coated SMS") with a chlorine dioxide-generating material. Upon exposure to activating conditions such as exposure to water and/or high humidity conditions, chlorine dioxide is released.

The chlorine dioxide-generating material may take a number of forms. For example, the material may include a hydrophobic phase containing an acid-releasing agent and a hydrophilic phase containing chlorite anions. When exposed to moisture, acid and hydronium ions are generated in the hydrophobic phase and the hydronium ions migrate to the hydrophilic phase. There, the hydronium ions react with the chlorite anions to release chlorine dioxide. Exemplary materials that may be utilized as the sterilant generator 9 in the present invention are also described in U.S. Pat. Nos. 5,360,609; 5,695,814; 5,707,739; 5,631,300; 5,668,185; and 5,705,092, all of which are incorporated herein in their entireties by reference thereto.

As mentioned earlier, the sterilant indicator will typically be in communication with the interior of the sterilization package. In some embodiments, the indicator strip may be attached to an interior transparent wall of bag 3 so as to remain visible during the sterilization process. Alternatively, the indicator material could form an integral portion of the package wall. It is also possible to position the indicator on the exterior of the package and adjacent a portion of the package wall permeable to chlorine dioxide so that the indicator may be acted upon by chlorine dioxide, or other sterilant, emanating from the sterilant generator 9. Such externally-carried indicators, however, should generally be attached to the container in a manner that maintains the aseptic properties of the sealed container.

In one particular embodiment, sterilization system 1 employs a chlorine indicator strip 13 which consists of strips of moistened chlorine indicator paper (sold under the name "pHydrion MICRO CHLORINE" by Micro Essential Laboratory, Inc.) that are placed within bag 3 prior to sealing. These particular indicator strips typically turn dark blue or black within 20 minutes after being exposed to chlorine dioxide.

In the Examples set forth below, the time indicator 15 employed was obtained from Temtec, Inc. of Suffrin, N.Y. This particular indicator is constructed according to the teachings of U.S. Pat. No. 5,699,326, which is incorporated herein in its entirety by reference thereto. These time indicators use a diffusion-controlled two-component system in which one part of a paper, printed with a special migrating ink, is combined with an adhesive-backed label. When the adhesive side is applied to the printed paper side, the adhesive dissolves the ink, and the timing process is initiated. The rate of ink diffusion through the adhesive and into the adhesive-backed label may be calibrated to correspond to any selected period of time. Accordingly, the appearance of color or pattern indicia on the indicator signals that the calibrated time period has elapsed.

A separate adhesive or other conventional attachment mechanism may be used to secure the time indicator to the sterilization package. The time indicator 15 will indicate an established elapsed time interval which can be verified by the user of the packaging apparatus. Typically, visual signals will be produced by the time indicator 15 and the sterilant indicator 13 to indicate to the user that the sterilant indicator 13 and the time indicator 15 have been fully activated. At that point, the user will know that the packaged materials have been sufficiently self-sterilized to allow their use in a sterile environment.

Figure 2:
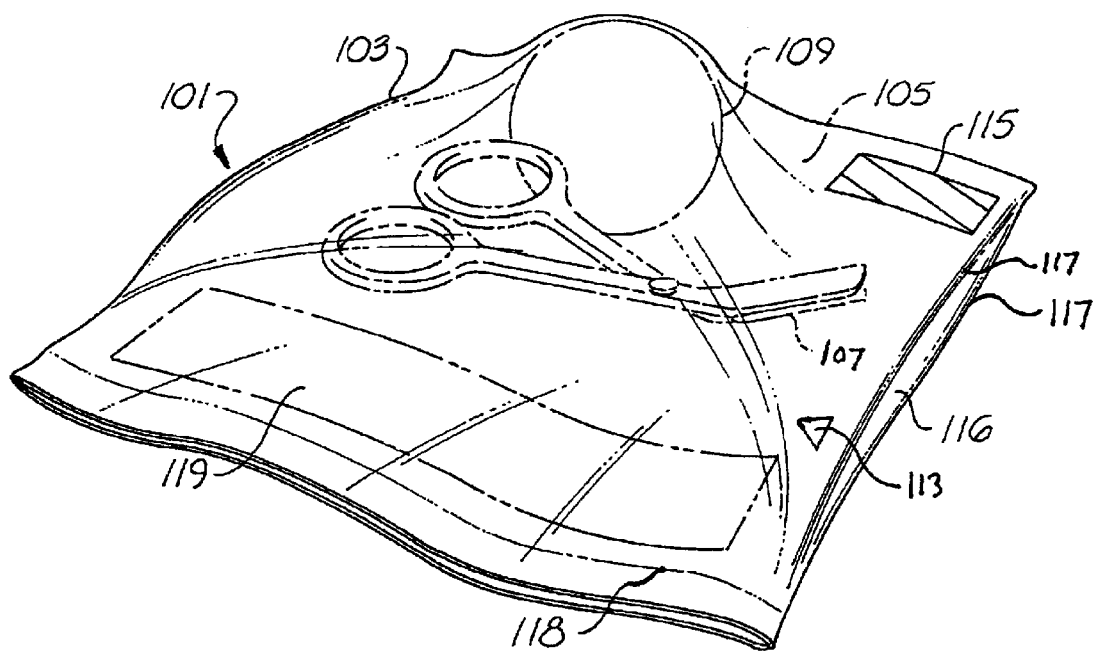
FIG. 2 is a perspective view of an additional embodiment of the present invention.

An additional embodiment of the present invention is shown as sterilization system 101 in FIG. 2. A container for a sterilized object 107 is depicted in the form of a reclosable rectangular pouch 103 which defines an opening 116 between unsealed margins 117. A continuous sealed edge 118 is defined by the remaining sides of the pouch. Time indicator 115 is placed in proximity to opening 116. A sterilant indicator 113 is placed within the interior of the pouch 103. The sterilant generator 119 (in this particular embodiment, a chlorine dioxide generator) is provided in the form of a coated region along the inner surface of the pouch 103. A sterilant activator 109, such as a humidifying agent, is placed on a side opposite the location of the sterilant generator 119. The relative placement of the sterilant generator 119 and the sterilant activator 109 may be advantageous in this particular embodiment due to the high affinity of chlorine dioxide for water.

Figure 3:
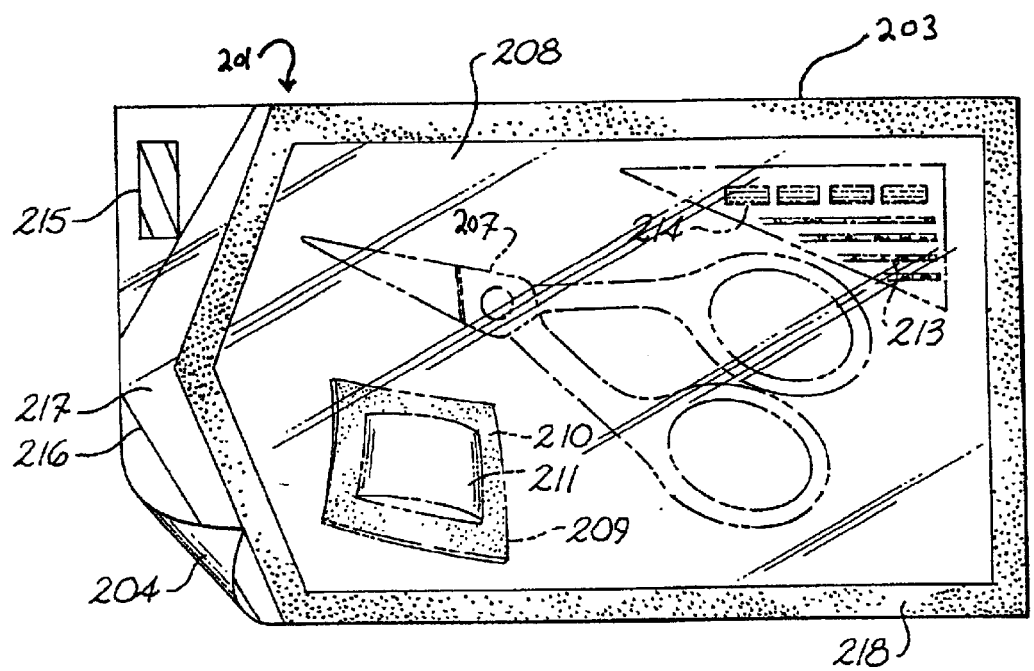
FIG. 3 is a perspective view of a peel-type sterilization pouch which sets forth additional variations in the packaging components.

An additional embodiment of the present invention is shown in FIG. 3. Packaging system 201 is provided as a container in the form of a peel pouch 203 having an upper transparent film layer 208 opposite a barrier backing 204. The peel pouch 203 is similar in construction to the peel pouch shown in U.S. Pat. No. 4,121,714, which is incorporated herein in its entirety by reference thereto. However, rather than a plain paper backing as utilized in the above reference, the backing 204 should have sufficient barrier properties to prevent the emanation of chlorine dioxide from the interior of the container. Such barrier properties may be provided by a wax coating, film layer, or other backing material which reduces the permeability of the paper to chlorine dioxide. Typically, such a peel pouch 203 will have a chevroned-shaped end which may be opened for removing sterilized instruments therefrom. For example, the pouch 203 may have a chevron-shaped flap 216 overlaying an unsealed margin 217 which may be pulled back by a user during opening to remove the sterilized articles. Typically, the instruments will have been placed into the peel pouch through the end 243 which is opposite flap 216 and which remains open until the instruments have been inserted and the end 243 has been adhesively sealed.

A sterilant generator 209 is placed inside the peel pouch 203. Time indicator 215 may be placed on peel pouch 203 and a sterilant indicator 213 may be placed within the interior of pouch 203. Sterilant indicator 213 may have a series of indicia 214 which provide visible indicators of exposure to varying concentrations of a sterilizing gas. In one embodiment, the sterilant generator 209 may be a chlorine dioxide chemical packet having a rupturable liquid-containing compartment 211 carried upon an absorbent matrix 210. When the acid contents of compartment 211 are combined with the chlorite absorbent component of matrix 210, chlorine dioxide gas is evolved from the generator. This embodiment of sterilant generator 209 may be manually ruptured to initiate the release of chlorine dioxide. The construction of such a generator is shown in U.S. Pat. No. 5,126,070 to Leifheit et al. which is incorporated herein in its entirety by reference thereto. When using a flexible sterilization container, such as a plastic bag or pouch, the generator 209 may be ruptured after sterilizable articles 207 have been placed inside the interior of the bag and the bag has been sealed.

Another embodiment of this particular generator 209 may employ a carbonate material that reacts with the acid to form carbon dioxide. The formation of carbon dioxide gas helps expel the chlorine dioxide from compartment 211 and assists in disbursing the chlorine dioxide within the interior of the sterilization container.

It should be appreciated that in this particular embodiment, the sterilant activator is not a humid-enhanced environment. Instead, activation of the sterilant generator 209 is caused by manually rupturing compartment 211 to expel the chlorine dioxide. "Manual" as referred to herein is meant to include various manipulations which result in a physical change to the sterilant generator and includes both human as well as mechanical intervention. For example, "manual" manipulation would include, but not be limited to, repositioning of the generator, tumbling of the generator/container in a particular machine, physically relocating the generator, as well as actually rupturing the generator to release the sterilant.

In embodiments where manual manipulation of the generator is utilized to release the sterilant, a humid environment within the interior of the self-sterilizable package may actually provide certain sterilizing benefits. Bacterial spores will hydrate in a humid environment and are thereafter more susceptible to the chemical treatment as discussed in U.S. Pat. No. 5,290,524 to Rosenblatt and U.S. Pat. No. 4,681,739 to Rosenblatt, both incorporated herein in their entireties by reference thereto. Further, given the high affinity of chlorine dioxide for water, a high humidity environment may improve the distribution of chlorine dioxide within the enclosure.

A series of experiments was conducted to determine effective parameters and conditions in which chlorine dioxide may be used in the sterilization of medical supplies in various embodiments of the present inventive packaging and process. The various experiments made use of spores of various Bacillus species as biological indicators in a vial form or as an applied spore solution of *Bacillus subtilus* (SPORTROL) in a concentration of $1.6 \times 10^6$ spores per 0.1 ml. The use of bacterial spore test data is widely recognized within the art as part of a validation protocol for sterilization techniques.

EXAMPLE 1

A surgical gown was used to evaluate the effectiveness of the chlorine dioxide-releasing formulations. The surgical gown was a reinforced, non-woven folded gown. Two biological indicator vials were located within the folded garment and two additional biological indicator vials were placed along the exterior of the gown. A piece of coated SMS, formulated to release 0.94 mmole of chlorine dioxide as described above with respect to sterilant generator 9, was used to loosely surround the folded gown using a C-fold. The surrounded gown was then placed within a 2 mil thick polyethylene bag. Silica fiber, having a saturated ammonium sulfate solution applied thereto, was used to increase the humidity. Electrochemical chlorine dioxide detectors were inserted through the polyethylene bag to evaluate chlorine dioxide levels in the center and exterior of the wrapped gown. Temperature and humidity probes were also positioned along the exterior of the wrapped gown. The polyethylene bag was heat sealed and left at ambient laboratory conditions for 47 hours.

The interior of the folded gown achieved a maximum chlorine dioxide concentration of 11 parts per million (ppm) after 20 hours of exposure and thereafter slowly decreased. The chlorine dioxide concentration on the outside of the folded gown peaked at 65 ppm over a 20 hour time interval. The relative humidity within the sealed bag increased to a level ranging from 47 through 55 percent throughout the test interval.

After 47 hours, the sealed bag was opened and the biological indicator vials were removed and incubated. The treated vials showed no growth following a 12-hour incubation period, while the unexposed control vials, not exposed to the chlorine dioxide, changed color to indicate spore growth. These results indicate that the coated SMS fabric released an effective amount of the chlorine dioxide gas to achieve sterilization conditions within the interior of a folded garment.

EXAMPLE 2

The chlorine dioxide releasing formulations were also evaluated in reference to an OthroArts VI surgical pack, Stock No. 88461 (available from Kimberly-Clark Corporation), which contains a folded surgical gown, towel, and surgical drapes. The biological indicators as used in Example 1 were placed within the center of the pack and along an exterior of the folded pack components. To increase the humidity, the surgical pack was partially unfolded and misted with water and refolded. The surgical pack was wrapped in a length of coated SMS fabric formulated to release 0.612 millimole of chlorine dioxide. The bag was heat sealed and left at ambient laboratory conditions for 21 hours after which time the bag was unsealed and the vial indicators removed and incubated. The indicators positioned along the exterior of the surgical pack showed no growth following incubation. The two biological indicators positioned at the center of the pack did show growth, as indicated by a color change, indicating that the sterilization process was not effective within the center of the surgical pack.

The lack of sterilization conditions within the pack interior was attributed to the combined effects of a lower concentration of chlorine dioxide at a shorter exposure interval, and a thicker, higher volume article being treated.

EXAMPLE 3

A surgical gown was evaluated using the materials and procedures set forth in Example 1. The coated SMS fabric was formulated to release 2.16 millimole of chlorine dioxide. The chlorine dioxide concentration reached a maximum value of 80 ppm after four hours. The relative humidity reached and maintained 100 percent after 30 minutes. Following a total treatment time of eight hours, the biological indicator vials were removed and incubated. Both the internally placed vials and the externally placed vials were tested and found to be sterile. Untreated control vials tested positive for bacterial growth.

The test data indicates that larger volume releases of chlorine dioxide can be achieved and may be effective in reducing the exposure time necessary to bring about complete sterilization. In particular, for bulky items such as fabrics, a higher concentration of released chlorine dioxide may facilitate the penetration of fabrics by the necessary amount of the chlorine dioxide sterilant gas.

EXAMPLE 4

A folded surgical gown was evaluated using the protocols outlined in Examples 1 and 3 above. Instead of being partially surrounded with a C-fold wrap of the coated SMS fabric, the folded gown was positioned between two sheets of coated SMS, each sheet capable of releasing a maximum of 0.141 millimoles chlorine dioxide. A maximum chlorine dioxide concentration of 40 ppm was achieved after three hours and slowly tapered off. Relative humidity reached 100 percent after 20 minutes and remained constant thereafter.

Following an exposure interval of eight hours, the sealed package was opened and the biological indicator vials were removed and incubated. When compared to untreated control vials, the treated biological indicator vials showed no color change following a 12 hour incubation. The data supported the use of multiple sheets of coated SMS as a chlorine dioxide generator, allowing placement of a sheet within a garment or in multiple locations within a package to bring about an improved release pattern of chlorine dioxide sterilant gas.

EXAMPLE 5

A lumen test device was constructed having a central portion designed to contain a biological indicator vial. The central portion was a four-inch length of tubing having a 0.75 inch outer diameter Each end of the tube was connected in a stepped down fashion to a 1.5 inch long, 0.625 inch outer diameter tube in turn connected to a 0.5 inch outer diameter tube having a length of 0.5 inches which was in turn connected to a 0.375 inch outer diameter tube having a 4 inch length. The overall length of the lumen test device was 12 inches. A biological indicator vial, as used in Examples 1 through 4, was placed at the central portion of the lumen test device. The lumen test device was placed inside a 10 inch by 12 inch polyethylene bag having an EVOH barrier ply designed to retard passage of chlorine dioxide gas through the bag walls. The lumen test device was sandwiched between two plies of coated SMS sheets formulated to release chlorine dioxide in the amounts used in Examples 1 through 4 above. Each bag was pre-moistened with a water spray mist and then sealed for intervals of 1, 2, or 4 hours. Following the appropriate time intervals, the vials were incubated and checked for color changes.

For each chlorine dioxide concentration evaluated, all the two-hour and four-hour exposure intervals to the chlorine dioxide gas provided complete sterilization of the vials. The indicators exposed to the lowest gas concentration (two sheets of 0.141 millimole chlorine dioxide-coated SMS) and for the 1 hour exposure interval failed to provide complete sterilization. The longer time intervals at the same concentration of chlorine dioxide were effective in sterilizing the indicator vials.

The results indicate that sterilization conditions are achieved by the interaction of the concentration of the sterilant and the corresponding time interval. Higher concentrations of sterilants, such as chlorine dioxide, provide a more rapid sterile environment. Lower concentrations of sterilants can provide suitable sterilization if the sterilizable objected are exposed to the sterilant over a longer exposure interval. Further, sterilizing gases, such as chlorine dioxide, can penetrate into recessed regions and lumens, an ability that might be important with respect to the sterilization of certain medical instrumentation.

EXAMPLE 6

Eight out of nine previously sterilized surgical clamps were inoculated with a 0.1 ml SPORTROL spore suspension containing *Bacillus subtilus* at a concentration of $1.6 \times 10^6$ spores per 0.1 ml. The ninth sterilized clamp that was not inoculated served as a "negative" control. The spore solution was applied to the hinge region of each clamp and allowed to dry overnight. Following drying, the inoculated clamps were closed, thereby occluding the inoculated area, and each clamp was individually heat sealed in a 10 inch by 12 inch polyethylene, EVOH-barrier, bag along with a moistened sheet of nine inch circular filter paper. Two inoculated clamps were left untreated as a positive control for the inoculation protocol. The remaining clamps were exposed for four hours using coated SMS fabric as described in Example 1. Four of the inoculated clamps were exposed to 190 moles$\times 10^6$ of chlorine dioxide. Two of the clamps were exposed to 960 moles$\times 10^6$ of chlorine dioxide. Following the four-hour exposure interval, the clamps were removed from the bags and tested for viable spores by immersion into a bacillus culturing media. All the chlorine dioxide-treated clamps were sterile. The negative control clamp, left uninoculated, tested negative for Bacillus spores. The positive controls (inoculated but not exposed to chlorine dioxide) indicated the presence of the Bacillus spores.

Additional testing, not separately set forth, has been used to evaluate packaging which incorporates a chlorine dioxide indicator such as the color indicator strips described above. Further, the packaging incorporated time indicators as previously discussed. It has been found that the combination of the time indicators and the chemical indicators provide a useful sterilization package. As the above results indicate, various combinations of time and chlorine dioxide concentrations are possible which provide efficacious results. The use of the respective indicators helps ensure that adequate sterilization conditions are provided for each package.

For instance, Examples 1–6 use a biological indicator which, upon exposure to spore culturing conditions, changes color when there is biological activity. Such indicators are useful for establishing effective chlorine dioxide concentrations, humidity levels, and exposure intervals for various size packages and for the various medical supplies contained therein. The Examples, along with additional testing using similar protocols, have indicated that a needed exposure time must be provided for proper sterilization. It is also apparent from test results that the necessary exposure interval and concentration of sterilant such as chlorine dioxide may need to be varied depending upon the package contents. For instance, a longer exposure time may be necessary for a surgical kit having a gown, towels, and surgical drapes than a surgical kit containing a single folded surgical gown. Routine experimentation using the protocols and Examples set forth above will allow quantification of various combinations of sterilizing agent concentration and exposure time intervals for any given set of materials or supplies. As a general rule, the lower the concentration of the sterilizing agent, the greater the exposure time that is required for sterilization.

An evaluation of the test results also suggests a strong correlation between a high humidity environment within the sealed package and the successful release of sterilizing agents such as chlorine dioxide. A moist environment of 80% relative humidity or higher was found to be operative with respect to the chlorine dioxide generators used and evaluated. Movement and manipulation of a pliable enclosure was also found to increase the distribution efficiency of the released gas within the enclosure.

The amount of chlorine dioxide, or other sterilant, needed will also vary depending upon the material of the container used in the packaging system. Materials used to make sterilizing bags and pouches are, to varying degrees, permeable to chlorine dioxide and other sterilizing agents. The thickness and/or presence of barrier materials may be used to minimize the diffusion rate of the chlorine dioxide. The use of glass or metal enclosures may be used to prevent appreciable diffusion losses altogether and to provide completely impermeable enclosures.

However, once sterilization has occurred, the diffusion of chlorine dioxide from the pouch or bag-type enclosures may be beneficial in that the chlorine dioxide will eventually "off-gas" from the sealed and sterile enclosure. As such, the enclosures and medical supplies therein require fewer handling precautions than materials having residues of more toxic chemical sterilizing agents. If desired, the selected time interval for the time indicator 15 may reflect an interval sufficient to allow the sterilant gas to off gas completely.

While the examples set forth above were directed to packaging containers using flexible and transparent bags, the present invention is also well-suited for use with other sterilization packaging such as those sterilizable by ethylene oxide and other sterilants.

Sealable rigid glass containers and chlorine dioxide-resistant plastic containers may also be used with the present invention. Any of the embodiments described herein or set forth in the accompanying figures may make use of several different forms of sterilant generators contemplated by this present application. The placement of the sterilant generator may be varied depending upon the type of container and the contents to be sterilized. Irrespective of the choice of a container, the container and container contents should be arranged in a manner which does not occlude or interfere with the release, circulation, or diffusion of the sterilant through the package. As set forth in some of the examples, more than one sterilant generator may be used within a package to increase the efficiency of sterilant distribution.

The activator, or triggering mechanism, for the sterilant generator may take several forms. One useful trigger includes a spray mist which may be applied to the container prior to sealing the sterilizable container. In addition, saturated filter paper and fabric webs may be used to provide a humidity source. In addition, ammonium sulfate solutions may be used on silica fibers or fabric webs to increase the humidity within the packages. Other activators or triggering mechanisms may be employed with specific types of sterilant generators. When an exterior source is utilized, a sterilant activator 19 as shown in the Figure then becomes unnecessary for proper operation of the system.

It is envisioned that a chemical release indicator may be utilized on the carrier material for the humidity source. It was noted during the above experiments that colored fabrics would bleach upon exposure to the chlorine dioxide. As such, the color change as reflected in the bleaching action would provide one type of an irreversible indicator demonstrating the release of the chlorine dioxide. It is also envisioned that a quantitative sterilant indicator may be provided in which the intensity or amount of color change correlates with the amount of released sterilant.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A system for sterilizing a sterilizable object, the system comprising:
   a container having an interior, said container having a sealable opening through which a sterilizable object may be placed into the interior of said container;
   a sterilant generator disposed within the interior of said container;
   a sterilant activator operative within the interior of said container; and
   an indicator adapted to indicate when sterilizing conditions have been achieved within the interior of said container;
   whereby, when a sterilizable object is placed within the interior of said container, and the opening of the container is sealed, the sterilant generator is activated by the sterilant activator to release an effective amount of sterilant within the interior of the container to sterilize said sterilizable object.

2. The system according to claim 1 wherein said indicator is adapted to indicate when an effective amount of sterilant has been generated.

3. The system according to claim 1 wherein said indicator is adapted to indicate when an effective time interval has elapsed.

4. The system according to claim 1 wherein said indicator indicates when an effective amount of sterilant has been generated and when an effective time interval has elapsed.

5. The system according to claim 1 wherein said sterilant generator generates chlorine dioxide gas when activated.

6. The system according to claim 1 wherein said sterilant activator comprises moisture.

7. The system according to claim 1 wherein said sterilant activator comprises manual manipulation of said sterilant generator.

8. A system for sterilizing a sterilizable object, the system comprising:
   a container having an interior and a sealable opening through which a sterilizable object may be placed;
   a sterilant generator that will produce an effective amount of chlorine dioxide gas, said sterilization generator being disposed within said container;
   a visual indicator in communication with the interior of the container, said visual indicator being responsive to the presence of the effective amount of chlorine dioxide gas;
   a time indicator disposed in communication with the container and adapted to indicate the passage of a predetermined time interval;
   wherein, when a sterilizable object is placed within the interior of the container and the opening is sealed, the generator releases an effective amount of chlorine dioxide within the container when said generator is activated, while a time indicator is activated to indicate when a sufficient time interval has elapsed.

9. The system according to claim 8, wherein the generator further comprises a carrier having a coating formulated to release an effective amount of chlorine dioxide.

10. The system according to claim 9 wherein said coating is a film.

11. The system according to claim 9, wherein the coating is formulated to release the effective amount of chlorine dioxide in the presence of at least about 80% humidity.

12. The packaging system according to claim 8 wherein the generator further comprises a composition applied to an inner surface of the container.

13. The packaging system according to claim 8 wherein a humidifier is disposed within the interior of the container.

14. The packaging system according to claim 8 wherein the generator further comprises a chlorine dioxide-releasing composition responsive to an internal package stimulus.

15. The packaging system according to claim 8 wherein the container is partially formed of a flexible film.

16. The packaging system according to claim 8 wherein the container is a sterilization pouch having an upper plastic member sealed along its margins to a lower paper member.

17. The packaging system according to claim 8 wherein the container is a rigid container.

18. The packaging system according to claim 17 wherein the rigid container is at least partially formed of glass.

19. The packaging system according to claim 17 wherein the rigid container is at least partially formed of plastic.

20. A process of sterilizing a sterilizable object comprising the steps of:
    supplying a sterilizable object to be sterilized;
    placing the sterilizable object within an interior of a sealable container;
    providing a generator of a sterilant within the container;
    sealing the sterilizable object within said container;
    activating a time indicator disposed on the container;
    activating said generator so as to release a sterilant from the generator, the sterilant reacting with a visible change indicator in communication with the interior of the container and responsive to the presence of an effective amount of the sterilizing gas; and
    maintaining the container in a sealed condition until sterilizing conditions have been achieved.

21. The process according to claim 20 wherein the step of releasing a sterilant comprises releasing a gas.

22. The process according to claim 21 wherein said gas is chlorine dioxide.

23. The process according to claim 20 wherein the step of providing a generator of a sterilant comprises providing a carrier having a coating formulated to release chlorine dioxide gas.

24. The process according to claim 20 wherein the step of providing a generator of a sterilant further comprises supplying a chlorine dioxide-generating composite coating carried by an inner wall of the container.

25. The process according to claim 20 further comprising the step of providing the time indicator to a location in proximity to the opening of the container.

26. The process according to claim 20 wherein the step of releasing a sterilant further comprises reacting the sterilant with a visible change indicator carried by an outer wall of the container as a portion of the sterilant passes through the outer container wall and in proximity to the visible change indicator.

27. The process according to claim 20 wherein the step of releasing a sterilant further comprises releasing the sterilant in response to an environmental condition within an interior of the container.

* * * * *